US012782334B2

(12) United States Patent
Foata et al.

(10) Patent No.: US 12,782,334 B2
(45) Date of Patent: Nov. 3, 2026

(54) STATE BASED OPERATION OF ELECTRICAL EQUIPMENT

(71) Applicant: Maschinenfabrik Reinhausen GmbH, Regensburg (DE)

(72) Inventors: Marc Foata, Regensburg (DE); Rainer Frotscher, Regenstauf (DE); Alexander Alber, Regensburg (DE); Markus Dolles, Regensburg (DE)

(73) Assignee: REINHAUSEN GMBH, Regensburg (DE)

( * ) Notice: Subject to any disclaimer, the term of this patent is extended or adjusted under 35 U.S.C. 154(b) by 195 days.

(21) Appl. No.: 18/722,630

(22) PCT Filed: Nov. 22, 2022

(86) PCT No.: PCT/EP2022/082715
§ 371 (c)(1),
(2) Date: Jun. 21, 2024

(87) PCT Pub. No.: WO2023/117251
PCT Pub. Date: Jun. 29, 2023

(65) Prior Publication Data

US 2025/0147002 A1 May 8, 2025

(30) Foreign Application Priority Data

Dec. 21, 2021 (DE) ..................... 10 2021 134 031.4

(51) Int. Cl.
*G01N 33/28* (2006.01)
*G01R 31/62* (2020.01)

(52) U.S. Cl.
CPC ......... *G01N 33/2841* (2013.01); *G01R 31/62* (2020.01)

(58) Field of Classification Search
CPC ........ G01N 33/00; G01N 33/26; G01N 33/28; G01N 33/2835; G01N 33/2841;
(Continued)

(56) References Cited

U.S. PATENT DOCUMENTS

2002/0116148 A1* 8/2002 Bertsch .............. G05B 23/0283
702/184
2006/0259277 A1* 11/2006 Fantana ................. G06Q 10/10
702/183
(Continued)

FOREIGN PATENT DOCUMENTS

CA 3088836 A1 * 7/2019 .............. H02J 13/13
CN 115358353 A * 11/2022 ............. G01D 21/02
(Continued)

OTHER PUBLICATIONS

Ivanka Hohlein-Atanasova et al., Carbon oxides in the interpretation of dissolved gas analysis in transformers and tap changers, IEEE Electrical Insulation Magazine, Nov. 2010, p. 22-26, vol. 26 Nr. 6, IEEE, USA, DOI: 10.1109/MEI.2010.5599976.

*Primary Examiner* — Hoai-An D. Nguyen
(74) *Attorney, Agent, or Firm* — LEYDIG, VOIT & MAYER, LTD.

(57) ABSTRACT

A method measures electrical equipment of a system for supplying power. The electrical equipment includes a housing with an insulating fluid. The method includes: recording measurement values representing dissolved gases in the insulating fluid; determining equipment parameters; adapting the measurement values to a uniform evaluation basis using the equipment parameters; assessing a state of the electrical equipment based on the adapted measurement values at least one machine learning method; and outputting the state.

19 Claims, 3 Drawing Sheets

(58) Field of Classification Search
CPC ........ G01R 31/00; G01R 31/50; G01R 31/62; H01H 9/00; H01H 9/0005; H01H 9/0044; H01H 2009/0061; H01H 33/00; H01H 33/02; H01H 33/53; H01H 33/56; H01H 33/567
USPC ................................ 324/500, 537, 551, 553
See application file for complete search history.

(56) References Cited

U.S. PATENT DOCUMENTS

| | | | |
|---|---|---|---|
| 2010/0005856 | A1 | 1/2010 | Cunningham |
| 2016/0282313 | A1 | 9/2016 | Robinson |
| 2022/0026385 | A1 | 1/2022 | Frotscher et al. |

FOREIGN PATENT DOCUMENTS

| | | | |
|---|---|---|---|
| DE | 102018131388 | A1 | 6/2020 |
| EP | 1217486 | A1 | 6/2002 |
| EP | 3073248 | A1 | 9/2016 |
| WO | WO 2004090764 | A1 | 10/2004 |
| WO | WO 2007115807 | A1 | 10/2007 |

* cited by examiner

STATE BASED OPERATION OF ELECTRICAL EQUIPMENT

CROSS REFERENCE TO RELATED APPLICATIONS

This application is a U.S. National Phase application under 35 U.S.C. § 371 of International Application No. PCT/EP2022/082715, filed on Nov. 22, 2022, and claims benefit to German Patent Application No. DE 10 2021 134 031.4, filed on Dec. 21, 2021. The International Application was published in German on Jun. 29, 2023 as WO 2023/117251 A1 under PCT Article 21 (2).

FIELD

The present disclosure relates to a system for supplying power based on a determined state of electrical equipment, method for determining the state of an item of electrical equipment of the system for supplying power, to an apparatus for determining the state of the item of electrical equipment of the system for supplying power.

BACKGROUND

In electrical power technology, a system for supplying power refers to a network for the transmission and distribution of electrical power. It consists of electrical lines, such as overhead lines and underground cables, as well as associated facilities such as power stations, substations and the equipment thereof.

Monitoring and analysing the state of an item of electrical equipment in a power supply system, such as a power transformer or tap changer, for example, is an important measure to ensure unimpeded operation of the power grid.

A proven method of inferring the state of a power transformer or tap changer is to analyse the insulating oil. Due to the natural ageing of the insulating oil, but especially due to thermal or electrical faults during operation, the insulating oil forms cracking gases, which are dissolved in the insulating oil. The amount and type of said dissolved gases, the rates of gas rise and the ratios of the gas types to one another can be used to indicate faulty operation of the equipment and even the type of fault. This analysis is known in the specialist field as so-called gas-in-oil analysis (DGA).

In addition to the natural ageing of the insulating oil and the faulty operation of an item of equipment, the equipment-specific parameters also play a decisive role in the gas generation and composition as well as the interpretation of the DGA data.

For example, a control transformer used in a substation has to meet different requirements to a transformer in a high-voltage DC transmission system. The same applies to an on-load tap changer that is designed in the respective transformer to adapt the winding ratio to the requirements of the respective field of application.

As a result, similar results from gas-in-oil analyses can also allow different conclusions to be drawn about the state of the equipment due to different equipment parameters. As a result, this may lead to an incorrect interpretation of the gas analysis and affect the assessment of the state of the electrical equipment.

SUMMARY

In an embodiment, the present disclosure provides a method that measures electrical equipment of a system for supplying power. The electrical equipment includes a housing with an insulating fluid. The method includes: recording measurement values representing dissolved gases in the insulating fluid; determining equipment parameters; adapting the measurement values to a uniform evaluation basis using the equipment parameters; assessing a state of the electrical equipment based on the adapted measurement values at least one machine learning method; and outputting the state.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
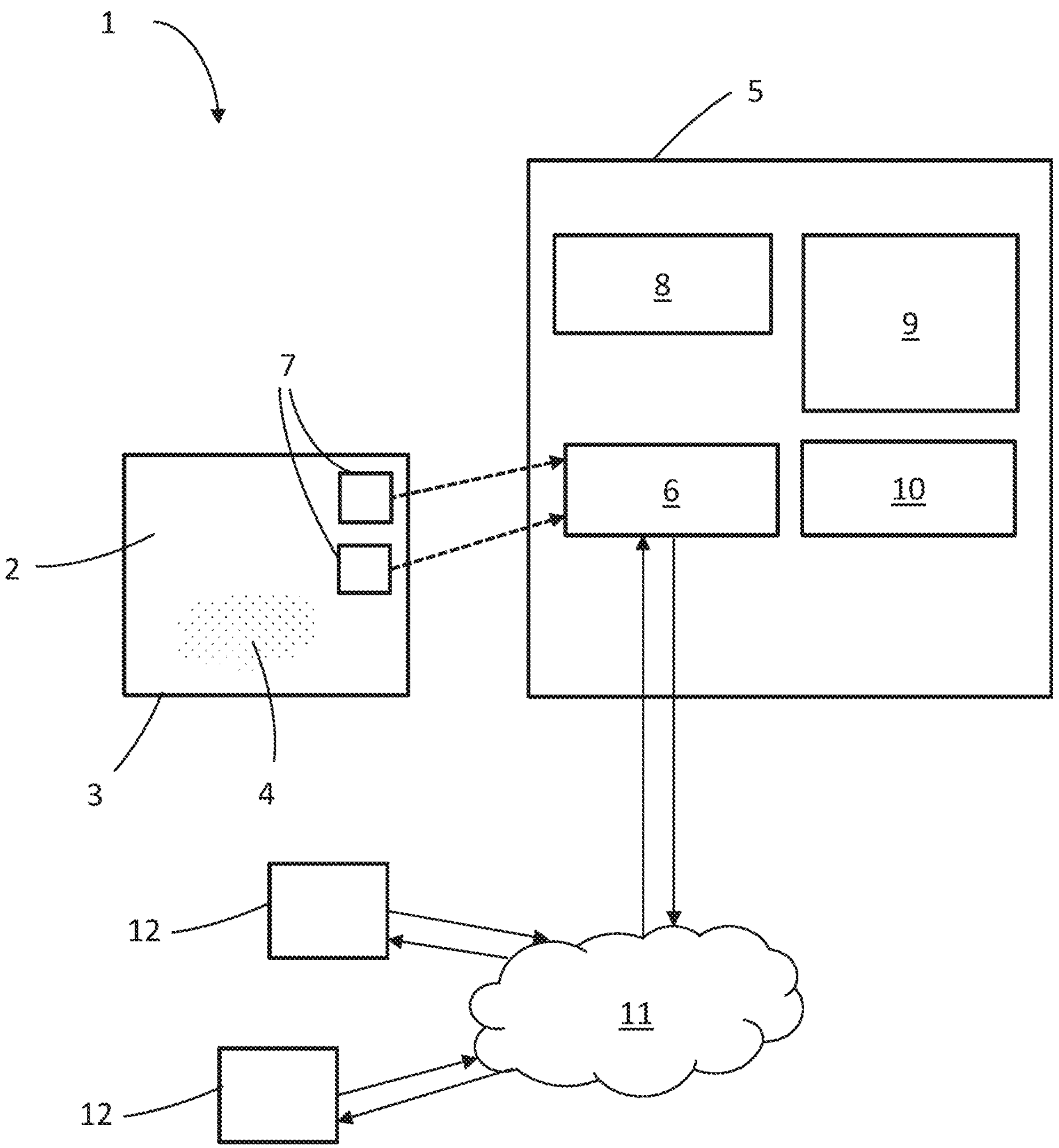
FIG. 1 shows a schematic illustration of an advantageous embodiment of a system for supplying power comprising an item of electrical equipment and an apparatus for analysing the state of the electrical equipment.

Aspects of the present disclosure provide an improved concept for state analysis of electrical equipment of a system for power supply that takes the specific parameters of the equipment into account in the analysis of the state and thus allows a more accurate evaluation of the state.

The improved concept is based on the idea of bringing the data received for the evaluation of the state to a uniform evaluation basis in order to enable a comparability of the individual equipment with a representative group of items of equipment and to achieve a more accurate interpretation of the DGA data based on this.

A first aspect of the improved concept specifies a method for analysing the state of an item of electrical equipment of a system for supplying power, wherein the electrical equipment comprises a housing with an insulating fluid. The method comprises the following steps:

- recording of measurement values representing dissolved gases in the insulating fluid,
- determination of equipment parameters,
- adaptation of the measurement values to a uniform evaluation basis by means of the equipment parameters,
- carrying out a state assessment of the electrical equipment based on the measurement values, which are adapted by means of the equipment parameters, by means of at least one machine learning method,
- determination of at least one state of the item of electrical equipment,
- outputting of the at least one state.

DGA data sets from DGA analyses carried out on the equipment are preferably used as measurement values representing dissolved gases in the insulating fluid.

In accordance with a preferred embodiment, in order to determine the measurement values, samples of the insulating fluid are taken and these are analysed in the laboratory. In this case, a current data set can be recorded as measurement values and/or one or more historical data sets can be recorded as measurement values.

In accordance with a further embodiment, the measurement values are recorded continuously, in particular at a regular time interval. For this purpose, for example, at least one sensor is provided for continuous measurement of the dissolved gases in the insulating fluid.

The insulating fluid is preferably in the form of an insulating oil.

In accordance with a preferred embodiment, the equipment parameters include structure-specific and design-specific parameters of the equipment, the operating principle of the equipment, the volume and the properties of the insulating fluid, the nature of the housing, the performance class, the operating mode of the equipment or the physical ambient conditions in which the equipment is located.

In accordance with a further embodiment, the equipment parameters are determined once.

In accordance with a further embodiment, the equipment parameters include, in particular, data sets that were determined during commissioning of the electrical equipment and/or during maintenance work on the equipment.

In accordance with a preferred embodiment, the recorded measurement values and/or the equipment parameters are checked for plausibility. This can be done by checking previously defined plausibility rules, which are based, for example, on defined limit values and/or value ranges. Known plausibility checking methods, such as "local outlier factor", for example, can also be used.

In accordance with a further embodiment, a probability of the validity of the at least one state of the electrical equipment is determined and the state is output with the validity probability.

In accordance with one embodiment, a first and a second state are output with the probability of the validity of the respective state. For example, the first state comprises a determined, fault-free state of the equipment and the second state comprises a determined, faulty state of the equipment.

In accordance with a further embodiment, three or more than three states are output with the probability of the validity of the respective state. For example, at least two of the states comprise at least two determined, different fault cases and at least one of the states comprises a determined, fault-free state.

In accordance with a further embodiment, the method comprises the following further steps:

determination of an indicator that indicates an uncertainty about the probability of the validity of the state, and outputting of this indicator.

In accordance with one embodiment, the indicator is in the form of a numerical value and/or a percentage value.

In accordance with a further embodiment, the uncertainty indicator is determined depending on the availability of the recorded measurement values and/or the determined equipment parameters.

If the indicator is in the form of a numerical value, in accordance with a preferred embodiment, the numerical value becomes larger as the availability of the recorded measurement values and/or determined equipment parameters decreases.

In accordance with a further embodiment, missing measurement values and/or missing equipment parameters are determined by means of at least one statistical evaluation method.

In accordance with a preferred embodiment, the missing measurement values are supplemented when the state evaluation is carried out.

In accordance with a further embodiment, the measurement values and the missing measurement values are adapted to a uniform evaluation basis by means of the equipment parameters and the missing equipment parameters.

In accordance with a further embodiment, the electrical equipment is in the form of a tap changer and the equipment parameters comprise, in particular, tap-changer-specific data.

In accordance with one embodiment, the tap-changer-specific data includes, for example, data concerning the switching number or switching frequency, the age, the volume of the insulating fluid, the typical load factor, the phase number, data concerning the basic structure and the design, the circuit topology or the operating principle of the tap changer. With regard to the operating principle, a distinction must be made, for example, between whether the tap changer is based on vacuum switching technology or on oil switching technology. In addition, tap-changer-specific data may also include data that was recorded during commissioning of the tap changer or during maintenance work.

In accordance with a further embodiment, in addition to the tap-changer-specific data, specific characteristic variables of the insulating fluid of the tap changer and/or the transformer and/or operational data of the tap changer and/or the transformer and/or transformer-specific data are determined. Operational data are understood to mean, in particular, the operating mode of the tap changer, for example the application in a hermetically sealed transformer, in mains operation, in a HVDC system or in a steelworks, or also the ambient conditions of the transformer and/or the tap changer.

The specific characteristic variables of the insulating fluid of the tap changer should be understood here to mean, for example, the distinction between a mineral oil, a synthetic or a natural oil, or also properties of the insulating fluid, such as the age, the proportion of inhibitors, passivators and/or other additives, for example.

In accordance with a further embodiment, the measurement values are additionally adapted to a uniform evaluation basis by means of the specific characteristic variables of the insulating fluid of the tap changer and/or the transformer and/or the operational data of the tap changer and/or the transformer and/or the transformer-specific data.

In accordance with a further embodiment, the statistical evaluation method for determining the missing measurement values and/or the missing equipment parameters is based on an imputation method, in particular on a singular and/or multiple imputation method and/or nearest-neighbour imputation method.

In accordance with a further embodiment, the machine learning method for carrying out the state assessment is based on a regression method and/or on a neural network and/or on a support vector machine and/or on a linear-discriminant analysis and/or on a Gaussian process regression.

In accordance with a further embodiment, the method comprises the following further step:

outputting of a status message and/or a warning message and/or a recommended action and/or carrying out an action relating to the operation of the electrical equipment depending on the determined state and/or the uncertainty indicator.

A second aspect of the improved concept furthermore specifies an apparatus for analysing the state of an item of electrical equipment of a system for supplying power, wherein the electrical equipment comprises a housing with an insulating fluid.

The features of the apparatus correspond to the steps of the method according to the first aspect of the improved concept. For the apparatus according to the second aspect of the improved concept, reference is therefore analogously made to the advantageous explanations, preferred features, technical effects and/or advantages that have already been explained for the method according to the first aspect and the corresponding embodiments of the method. There is no repetition.

The apparatus comprises an interface for recording measurement values representing dissolved gases in the insulating fluid and/or for recording equipment parameters.

The interface may be designed for automated and continuous recording of measurement values and/or equipment parameters, for example from sensors arranged on the electrical equipment.

Likewise, the interface may be in the form of an input unit for the manual recording of measurement values and/or equipment parameters.

Likewise, the interface may be designed for recording historical measurement values and/or equipment parameters from a higher-level network.

The apparatus further comprises an evaluation unit which is designed to carry out a method which is designed in accordance with the first aspect of the improved concept.

In accordance with one embodiment, the apparatus further comprises an output unit which is designed to output at least one state of the electrical equipment.

In accordance with one embodiment, the output unit is furthermore designed to output an indicator that indicates an uncertainty about a probability of the validity of the state.

The output is preferably implemented visually in the form of a graphical representation.

In accordance with a third aspect of the improved concept, a system for supplying power is also specified, comprising at least one item of electrical equipment and at least one apparatus for the state analysis of the at least one item of electrical equipment, which apparatus is designed in accordance with the second aspect of the improved concept.

Further embodiments and implementations of the system are directly evident from the various embodiments of the method and the apparatus.

The present disclosure is explained below in detail on the basis of exemplary embodiments with reference to the drawings. Components which are identical or functionally identical or which have an identical effect may be provided with identical reference signs. Identical components or components with an identical function are in some cases explained only in relation to the figure in which they first appear. The explanation is not necessarily repeated in the subsequent figures.

FIG. 1 shows a schematic illustration of an advantageous embodiment of a system for supplying power comprising an item of electrical equipment 2 and an apparatus 5 in accordance with the improved concept.

The system 1 comprises a tap changer 2, which in this case represents the electrical equipment and is provided for switching over between winding taps of a transformer. In addition to the tap changer 2 and the transformer, the system 1 comprises a plurality of electrical lines and the associated facilities such as power stations, substations and the equipment thereof for the transmission and distribution of electrical power. For the purpose of better clarity, however, only the essential components of a system 1 for supplying power for the improved concept are shown in FIG. 1.

The tap changer 2 comprises a housing 3, which is filled with an insulating fluid 4. Furthermore, the system 1 comprises an apparatus 5, which is provided for carrying out a state analysis of the tap changer 2. The apparatus 5 has an interface 6, via which measurement values relating to the tap changer 2 are transmitted to the apparatus 5. To record the measurement values, the tap changer 2 comprises at least one suitable sensor 7, which transmits the recorded measurement values to the apparatus 5 via the interface 6. The measurement values include, in particular, dissolved gases in the insulating fluid 4. In accordance with this, at least one sensor 7 is in the form of a DGA sensor. In addition, further measurement values in the form of real-time data of the tap changer 2, such as the system voltage, the load current, the operating time, the torque, the torque curve, the tap position, switching times, the number of approached positions or winding taps and the respective dwell time in a position, the temperature of the insulating fluid 4, the ambient temperature or other data regarding the tap changer 2 are recorded and taken into account in the state analysis. Depending on the type of measurement value, the recording can be carried out once or at regular intervals and can be transmitted automatically by means of the interface 6 via the corresponding sensors 7 or via a manual input to the apparatus 5. Tap-changer-specific parameters, such as the switching number or switching frequency, the age, the volume of the insulating fluid, the load factor, the phase number, data regarding the basic structure and the design, the circuit topology or the operating principle of the tap changer, or additional data, which were acquired during commissioning of the tap changer or during maintenance work, are optionally also incorporated in the state analysis of the tap changer 2. In addition, specific characteristic variables of the insulating fluid 4 of the tap changer 2, operational data of the tap changer 2, that is to say data dependent on the field of application of the tap changer, or transformer-specific parameters, such as data concerning the structure or the design of the transformer, can be taken into account in the state analysis. The parameters are stored in a data memory 8 of the apparatus 5. In addition, further data required for a plausibility check of the incoming measurement values and tap-changer-specific parameters carried out in the context of the state analysis can be stored in the data memory 8. For example, suitable plausibility rules, limit values, value ranges or program codes for the automated execution of the plausibility check can be stored in the data memory 8 accordingly.

The apparatus 5 further comprises an evaluation unit 9 which is designed to carry out the state analysis on the tap changer 2 using one or more machine learning methods and to output the state of the tap changer 2 via an output unit 10. Furthermore, the evaluation unit 9 is designed to carry out within the state analysis an automated plausibility check of the recorded measurement values by means of the tap-changer-specific parameters and to bring the recorded measurement values to a uniform evaluation basis by means of the tap-changer-specific and/or transformer-specific parameters and/or specific characteristic values of the insulating fluid and/or operational data. In addition, the evaluation unit 9 is set up to determine missing measurement values and/or missing tap-changer-specific or transformer-specific parameters using suitable, statistical evaluation methods. The missing measurement values are then supplemented when the state assessment is carried out. The missing tap-changer-specific or transformer-specific parameters are used to adapt the completed measurement values to a uniform evaluation basis, for example to a standard application of a tap changer in the network.

The described functionalities of the evaluation unit 9 can be implemented by hardware, firmware, software, other machine-readable command codes or a combination thereof.

The apparatus 5 for state analysis can also be connected to a higher-level network or the Internet 11 via the interface 6. The outputting of the state can then, as explained above, take place locally on the apparatus 5 via the output unit 10 or via the higher-level network 11 as a communication medium on various other terminal devices connected to the network 11. Another advantage of connecting to a higher-level network 11 is the access to further data from electrical equipment 12 which are also connected to the higher-level network, or access to historical DGA data of the equipment 2, which were transmitted to the network 11 via the interface 6 after recording. The historical measurement values and/or the data of the equipment 12 can be incorporated into the state analysis or used, for example, to adapt the measurement values to a uniform evaluation basis or to determine and supplement missing measurement values and parameters. It is also possible to transfer the performance of the state analysis, that is to say the functionalities of the evaluation unit 9, via this connection entirely to a server, a cloud or another computing device connected to the higher-level network or the Internet 11.

Figure 2:
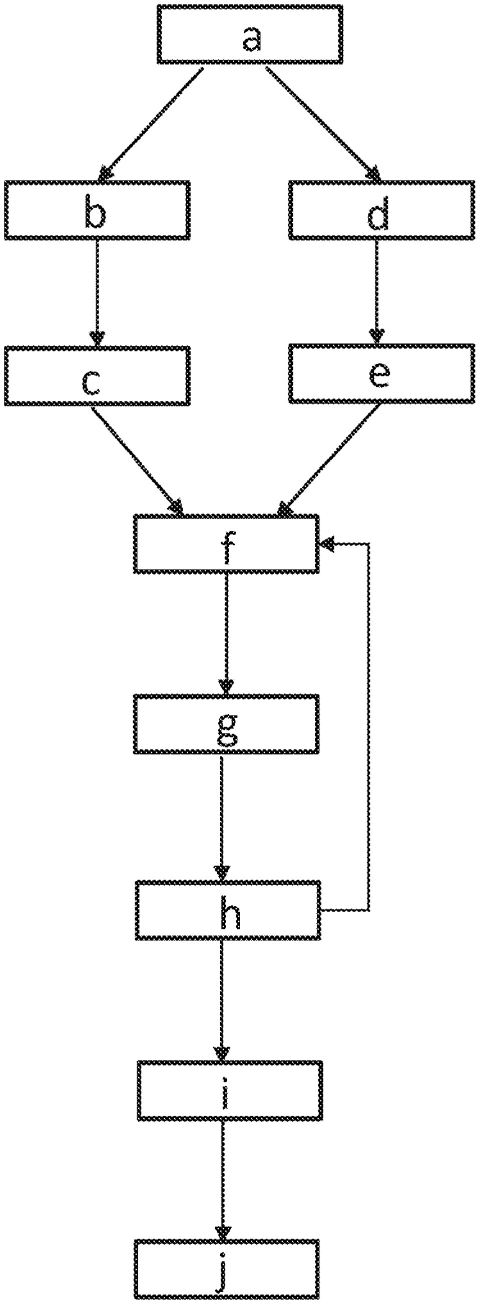
FIG. 2 shows one advantageous embodiment of the method in accordance with the improved concept.

FIG. 2 illustrates one advantageous embodiment of the method in accordance with the improved concept in the form of a flowchart.

In accordance with this advantageous embodiment, the method is used to analyse the state of an item of electrical equipment of a system for supplying power, as is shown, for example, in FIG. 1. Accordingly, the system 1 comprises at least one item of electrical equipment, which is in the form of a tap changer 2 and a housing 3 with an insulating fluid 4.

In accordance with a step a of the method, measurement values representing dissolved gases in the insulating fluid are first recorded. Typically, this is data that has been determined in the context of a gas-in-oil analysis. In a step b, equipment parameters are determined, wherein, in accordance with this embodiment, the equipment parameters are in the form of tap-changer-specific parameters, since the electrical equipment is a tap changer. In a step c, further data concerning the tap changer, namely the specific characteristic variables of the insulating fluid, such as the chemical composition and the properties of the insulating fluid, data relating to the field of application of the tap changer, and optionally also data concerning the transformer in which the tap changer is installed, are determined. The recorded data are checked for plausibility in a step d, for example by means of suitable plausibility rules, stored limit values or value ranges or program codes that carry out an automated plausibility check. In a step e, missing measurement values are determined by means of at least one suitable imputation method.

The sequence in which steps b, c, d, and e are carried out is irrelevant to the execution of the method. Steps d and e may be carried out, for example, after step a, step b or step c, or in parallel with steps b and c, as shown in FIG. 3.

In a next step f, the missing tap-changer-specific data are now also determined by means of at least one suitable imputation method. Then, in a step g, the measurement values recorded in step a and, if necessary, supplemented in step e are adapted to a uniform evaluation basis by means of the tap-changer-specific parameters determined in step b, and, if necessary, supplemented in step f, as well as the data additionally determined in step c, in particular the insulating fluid and the application case of the tap changer. For example, the measurement values can be adapted to a defined standard application in order to make the individual tap changer comparable to other tap changers. This allows better interpretation of the data and, consequently, improved evaluation of the state of the tap changer.

The state is then assessed in a next step h, based on the measurement values recorded, adapted in step e and optionally supplemented in step f as well as the other data recorded in step c by means of at least one machine learning method, for example by means of a support vector machine. Steps f, g, and h are repeated as often as desired, for example a thousand times, in this order.

Subsequently, depending on the state assessment in a step i, several possible states of the tap changer with a respective probability of the validity thereof and an indicator indicating an uncertainty with regard to the probability of the validity of the respective state are determined. Finally, the states are output together with the probability and the uncertainty indicator in a step j of the method. Optionally, appropriate warning messages and recommended actions can be issued for the operator of the tap changer with the output and depending on the state assessment, or actions can even be carried out automatically on the tap changer, for example blocking of the drive.

Figure 3A:
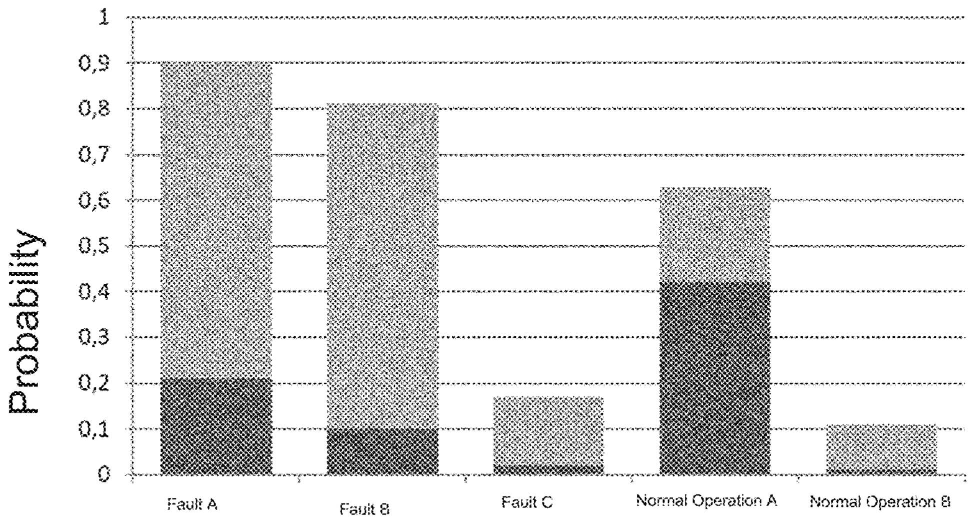
FIG. 3 shows an exemplary illustration of an output of a state of the electrical equipment.
Figure 3B:
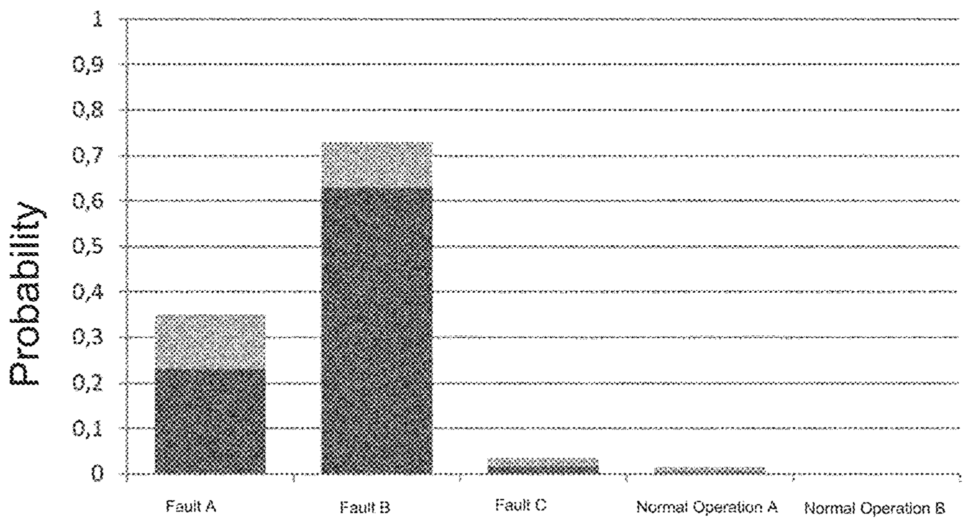

A possible representation of the output carried out in step j is shown in FIGS. 3*a* and 3*b*. A respective graphical representation in the form of two bar charts is shown. The states of the tap changer are plotted along the x axis. Each bar represents a possible state. In this example, a total of five states have been identified, namely “Fault A”, “Fault B”, “Fault C, “Normal operation A” and “Normal operation B”. For example, “Fault A” means the occurrence of one or more arcs, “Fault B” means the occurrence of one or more partial discharges in the on-load tap changer, and “Fault C” means, for example, the occurrence of impermissible heating states. In “Normal operation A”, the on-load tap changer is assumed to be in a fault-free state. “Normal operation B” in the present example means a state that refers to so-called “stray gassing”, an undesired formation of gas due to interactions between the insulating fluid and mostly metallic components of the on-load tap changer at normal operating temperatures. However, as stray gassing does not cause any consequential damage to the equipment to a certain extent, this state is not interpreted as a fault.

The probability of the validity of the respective state is plotted along the y axis. The height of the bars thus indicates the probability of the validity of a state.

FIG. 3*a* shows a presentation of results in which, compared to the representation in FIG. 3*b*, less measurement data and/or fewer equipment parameters which have been incorporated into the state evaluation were known. From FIG. 3*a* it can consequently be seen that the state “Fault A” is present with a probability of at least 20 percent. The area of the bars which is less highlighted in colour represents the indicator that indicates the uncertainty about the probability of the validity of the respective state. Taking the uncertainty indicator into account, the probability of the “Fault A” state being valid is between 20 and 90 percent. The value of the uncertainty indicator is therefore 70 percent. In comparison, FIG. 3*b* shows that the state “Fault A” is valid with a probability of at least 25 percent, wherein here the proportion of the uncertainty indicator is considerably lower, namely 10 percent. The probability of the validity of the “Fault A” state is therefore between 23 and 33 percent.

Accordingly, the remaining bars and accordingly the states "Fault B", "Fault C", "Normal operation A" and "Normal operation B" of FIGS. 3*a* and 3*b* must be interpreted in the same way.

The comparison of the two graphs illustrates the dependence of the uncertainty indicator on the availability of the measurement data and equipment parameters taken into account. In specific terms, this means that the more data is available and included in the state analysis, the lower the uncertainty is when it comes to indicating the probability of the validity of a state.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCE SIGNS

1 System for power supply
2 Item of electrical equipment, tap changer
3 Housing
4 Insulating fluid
5 Apparatus
6 Interface
7 Sensor
8 Data memory
9 Evaluation unit
10 Output unit
11 Network
12 Other item of equipment

The invention claimed is:

1. A method for measuring an electrical equipment of a system for supplying power, the electrical equipment comprising a housing with an insulating fluid, the method comprising:

recording measurement values representing dissolved gases in the insulating fluid;

determining equipment parameters specific to the electrical equipment;

adapting the measurement values to a uniform evaluation basis using the equipment parameters;

assessing a state of the electrical equipment based on the adapted measurement values using at least one machine learning method; and outputting the state.

2. The method according to claim 1, the method further comprising:

checking the recorded measurement values or the equipment parameters for plausibility.

3. The method according to claim 1, the method further comprising:

determining a probability of a validity of the state of the electrical equipment, wherein the state is output with the validity probability.

4. The method according to claim 1, wherein the method further comprises:

determining an indicator that indicates an uncertainty about the probability of the validity of the state; and outputting the indicator.

5. The method according to claim 4, wherein:

the uncertainty indicator is determined depending on an availability of the recorded measurement values or an availability of the equipment parameters.

6. The method according to claim 1, wherein:

missing measurement values or missing equipment parameters are determined by at least one statistical evaluation method.

7. The method according to claim 1, wherein:

the electrical equipment is a tap changer and the equipment parameters comprise tap-changer-specific data.

8. The method according to claim 7, wherein:

in addition to the tap-changer-specific data, specific characteristic variables of the insulating fluid or operational data or transformer-specific data are determined.

9. The method according to claim 8, wherein:

the measurement values are additionally adapted to a uniform evaluation basis by the specific characteristic variables of the insulating fluid or the operational data or the transformer-specific data.

10. The method according to claim 1, wherein:

the statistical evaluation method for determining the missing measurement values or the missing equipment parameters is based on an imputation method.

11. The method according to claim 1, wherein:

the machine learning method for carrying out the state assessment is based on a regression method, a neural network, a support vector machine, a linear-discriminant analysis, or on a Gaussian process regression.

12. The method according to claim 1, wherein the method further comprises:

outputting a recommended action or carrying out the recommended action relating to the operation of the electrical equipment depending on the determined state and/or the uncertainty indicator.

13. The method according to claim 1, wherein outputting the state comprises outputting a plurality of states, each with a respective indicator that indicates an uncertainty about the probability of the validity of the respective state.

14. The method according to claim 13, wherein the method further comprises displaying a warning message and recommended action based on the output states the respective indicator.

15. An apparatus for analysing a state of electrical equipment of a system for supplying power, the electrical equipment comprising a housing with an insulating fluid, the apparatus comprising:

an interface for recording measurement values representing dissolved gases in the insulating fluid and/or equipment parameters;

an evaluation unit, which is designed to carry out the method according to claim 1.

16. The apparatus according to claim 15, further comprising:

an output unit, which is designed to output a state of the electrical equipment.

17. The apparatus according to claim 15, wherein:

the output unit is furthermore designed to output an indicator that indicates an uncertainty about the probability of the validity of the state.

18. A system for supplying power, the system comprising:

at least one item of electrical equipment; and the apparatus for analysing the state of the electrical equipment according to claim 13.

19. A method for controlling an electrical equipment of a system for supplying power, the electrical equipment comprising a housing with an insulating fluid, the electrical equipment being at least one of a tap-changer or a transformer, the method comprising:

recording measurement values of the electrical equipment, at least one of the recorded measurement values representing dissolved gases in the insulating fluid;

determining equipment parameters specific to the electrical equipment, the equipment parameters comprising a plurality selected from the group consisting of: structure specific parameters of the electrical equipment, design specific parameters of the electrical equipment, a volume of the insulating fluid, a property of the insulating fluid, a nature of the housing, a performance class of the electrical equipment, an operating mode of the electrical equipment, and a physical ambient condition in which the electrical equipment is located;

adapting the measurement values into a uniform evaluation basis, the adapting being performed based on the determined equipment parameters for the electrical equipment and a predefined standard application;

determining a state of the electrical equipment based on the adapted measurement values using at least one of a regression method, a neural network, a support vector machine, a linear-discriminant analysis, or a Gaussian process regression; and outputting a recommended action or carrying out the recommended action relating to the operation of the electrical equipment depending on the determined state.

* * * * *